United States Patent [19]

Campolmi et al.

[11] 4,333,882
[45] Jun. 8, 1982

[54] PROCESS FOR PREPARING N-METHYLCARBAMATE OF METHYLTHIOACETALDOXIME

[75] Inventors: Stefano Campolmi, Novara; Vittorio Carletti, Meda; Marcello Marchi, Novara, all of Italy

[73] Assignee: Montedison S.p.A., Milan, Italy

[21] Appl. No.: 234,842

[22] Filed: Feb. 17, 1981

[30] Foreign Application Priority Data

Feb. 18, 1980 [IT] Italy .............................. 19979 A/80

[51] Int. Cl.³ ........................................... C07C 119/18
[52] U.S. Cl. .................................................. 260/453.3
[58] Field of Search ...................................... 260/453.3

[56] References Cited
U.S. PATENT DOCUMENTS 3,576,834  4/1971  Buchanan ........................ 260/453.3

FOREIGN PATENT DOCUMENTS 1521784  5/1967  France ............................. 260/453.3
1138347  1/1969  United Kingdom ............. 260/453.3

*Primary Examiner*—Henry R. Jiles
*Assistant Examiner*—Robert C. Whittenbaugh

[57] ABSTRACT

A process is disclosed for preparing N-methylcarbamate of methylthioacetaldoxime, characterized in that an aqueous suspension of methylthioacetaldoxime is additioned, in one step only, with gaseous phosgene and aqueous methylamine in the presence of an inorganic alkaline base substantially at room temperature and pressure.

The product obtained, known commercially as "Methomyl", is an important active principle in the field of insecticides.

9 Claims, No Drawings

PROCESS FOR PREPARING N-METHYLCARBAMATE OF METHYLTHIOACETALDOXIME

BACKGROUND OF THE INVENTION

N-methyl-carbamate of methylthioacetaldoxime of formula (I):

$$CH_3-\underset{\underset{SCH_3}{|}}{C}=N-O-\underset{\underset{O}{\|}}{C}-NH-CH_3 \quad (I)$$

is generally described in literature as obtained by reacting methylthioacetaldoxime of formula (II):

$$CH_3-\underset{\underset{SCH_3}{|}}{C}=NOH \quad (II)$$

with methylisocyanate of formula (III):

$$CH_3NCO \quad (III).$$

Such process has the drawback of requiring the use of methylisocyanate (III), a compound in itself not easily available on the market or prepared, in its turn, through a complex synthesis in gaseous phase conducted in apparatuses the industrial operation of which is burdensome.

A synthesis of N-methyl-carbamate of methylthioacetaldoxime (I), along with other homologs, by reaction of methylthioacetaldoxime (II) with sodium hydride and by successive reaction of the corresponding sodium salt with dimethylcarbamoyl chloride or with phosgene and ammonia, has also been described.

Such process is conducted in two consecutive steps. Furthermore, the preparation of the sodium salt of methylthioacetaldoxime involves the use of sodium hydride, i.e., of a reagent difficult to handle in expensive solvents (tetrahydrofuran).

In conclusion, the technique described hereinabove is characterized by the use of burdensome—as to costs and operation—reagents and conditions, which adversely affect its industrial application in general.

THE PRESENT INVENTION

An object of the present invention is to provide a simple and economical process for preparing N-methyl-carbamate of methylthioacetaldoxime having formula (I), which is free from the drawbacks of the prior art processes.

This and still other objects, which will more clearly appear to a technician skilled in the art from the following description, are achieved, according to the present invention, by a process for preparing N-methyl-carbamate of methylthioacetaldoxime having formula (I), characterized in that an aqueous dispersion of methylthioacetaldoxime of formula (II) is additioned, in one step only, with gaseous phosgene and aqueous methylamine, in the presence of an aqueous inorganic alkaline base, substantially at room temperature and pressure.

According to a particular feature of the present invention, particularly high conversion and selectivities in the desired product are achieved by operating at a constant pH approximately ranging from 8 to 12, preferably from 9 to about 10.

The reaction can be schematically represented by the following equation:

$$CH_3-\underset{\underset{SCH_3}{|}}{C}=N-OH + COCl_2 + CH_3NH_2 \xrightarrow{MOH}$$

$$CH_3-\underset{\underset{SCH_3}{|}}{C}=N-O-\underset{\underset{O}{\|}}{C}-NH-CH_3 + 2HCl,$$

wherein M is an alkaline metal selected from Na and K.

More specifically, the process consists in reacting the oxime (II) dispersed in water, at atmospheric pressure and at a temperature ranging approximately from 0° to 40° C., preferably at about 20° C., with phosgene, which is bubbled into the oxime (II) suspension, simultaneously with a gradual addition of an aqueous solution of an inorganic alkaline base, usually sodium hydrate, and of methylamine.

In other words, according to an unexpected characteristic of this invention, to obtain the best conversion and selectivity values, the reaction is conducted in one step only according to which the aqueous oxime (II) brought to the desired temperature is simultaneously and gradually additioned with the aqueous solution containing methylamine and the inorganic base, and with phosgene by bubbling, keeping the pH within the desired values. Said procedure is to be considered as critical to obtaining high yields and conversions.

In fact, if it is operated otherwise, for example by bubbling phosgene into a solution of the oxime in water containing the inorganic base and the methylamine, substantially less interesting results are obtained, as has been established experimentally.

The pH is maintained constant around a value between 8 and 12, preferably between about 9 and 10.

Bubbling of phosgene is stopped when the pH value is close to 7; on the average, the reaction is concluded after about 1 hour.

The molar ratio between the inorganic alkaline base and the oxime (II) may range from approximately 1:1 to 4:1, being preferably maintained around 3:1, while the molar ratio between methylamine and oxime (II) may vary from 1:1 to 3:1, being preferably maintained around 2:1.

The inorganic alkaline base can be indifferently selected from the sodium and/or potassium aqueous hydrates.

The starting methylthioacetaldoxime:

$$CH_3-\underset{\underset{SCH_3}{|}}{C}=N-OH \quad (II)$$

can be obtained, according to the art, by chlorination of acetaldoxime, followed by reaction of the resulting chloroacetaldoxime with sodium methylmercaptide.

Indicatively, by operating according to the parameters of the present invention it is possible to obtain results which, with conversions on the starting oxime higher than 98%, provide selectivity values in the desired product around 99%, provided the reaction is conducted under optimum conditions.

According to an effective embodiment, the process is conducted as follows.

Oxime (II) in an aqueous suspension is introduced into a thermoregulated reactor equipped with a stirrer, a thermometer, a gas scrubber, a dropping funnel and a pH measuring device.

Successively, under intense stirring, phosgene is bubbled in at the same time as an aqueous solution of the selected inorganic alkaline base and of methylamine starts dripping. After having kept the pH constant at about 9–10, when the alkaline and amine solution has stopped dripping, a further addition of phosgene lowers the pH to about 7. Bubbling of phosgene is then stopped. On the average, such operation takes on the whole about 1 hour. The reacting system is further stirred for about 30 minutes.

The resulting product is then separated by extraction with an organic solvent, etc.

Due to the mild operating conditions and to the high selectivity in the product obtained, this process appears particularly advantageous.

The process will be now described more in detail in the following examples, which are given, however, merely for illustrative, and not limiting, purposes.

Comparative Example 6 proves that the procedure according to the present invention is critical.

EXAMPLE 1

50 cc of distilled water and 5.3 g of methylthioacetaldoxime (II) were charged into a 250-cc flask equipped with a mechanical agitator, a thermometer, a dropping funnel, a scrubber and a pH measuring device.

Keeping the suspension under intense agitation, at a temperature of about 20° C. and at atmospheric pressure, bubbling of phosgene began simultaneously with dripping in of a solution consisting of 30 cc of distilled water, 6 g of NaOH and 9 cc of methylamine in water at 35% by weight. The two combined operations were such as to maintain the pH constantly around 9–10.

When the basic solution stopped dripping and the pH value reached 7, 9 g of phosgene as a whole in about 40 minutes were fed. After a further 20-minute agitation, the resulting aqueous suspension was extracted with three portions of 50 cc of methylene chloride. The organic phase was dried on sodium sulphate and evaporated to dryness. 8.2 of a white solid having a content of N-methyl-carbamate of methylthioacetaldoxime (Methomyl) (I) equal to 96% were obtained.

EXAMPLE 2

By operating as in Example 1 and using 4 g of soda and 7 g of phosgene, 8 g of a white solid having a Methomyl content of 92% were finally obtained.

EXAMPLE 3

By operating as in Example 1 and employing 6 cc of an aqueous solution of methylamine at 35% by weight and 7.5 g of phosgene, 8 g of a white solid having a Methomyl content of 90% were obtained.

EXAMPLE 4

By operating as in Example 1 and maintaining a temperature of about 0° C., 8.1 g of a white solid having a Methomyl content of 75% were obtained.

EXAMPLE 5

By operating as in Example 1 and keeping a temperature of about 40° C., 8.0 g of a white solid having a Methomyl content of 88% were obtained.

EXAMPLE 6 (Comparative)

Utilizing the apparatus described in Example 1, 5.3 g of methylthioacetaldoxime (II), 70 cc of distilled water, 6 g of NaOH and 9 cc of an aqueous solution at 35% by weight of methylamine were charged all together into the reactor. Keeping the temperature at about 20° C., 8.5 g of phosgene were bubbled in 40 minutes until a final pH value of 7 was attained. The pH of the solution remained close to 14 for about ¾ of the bubbling time.

After separation, 7.5 g of a white solid having a Methomyl content of only 61% were obtained.

What we claim is:

1. A process for preparing N-methylcarbamate of methylthioacetaldoxime of formula $$CH_3-\underset{\underset{SCH_3}{|}}{C}=N-O-\underset{\underset{O}{\|}}{C}-NH-CH_3 \qquad (I)$$

characterized in that an aqueous suspension of methylthioacetaldoxime of formula $$CH_3-\underset{\underset{SCH_3}{|}}{C}=NOH \qquad (II)$$

is additioned, in one step only, with gaseous phosgene and aqueous methylamine in the presence of an aqueous inorganic alkaline base, substantially at room temperature and pressure, and at a pH maintained constant around a value between 8 and 12.

2. The process of claim 1, characterized in being conducted at a pH maintained constant at a value around 9 and 10.

3. The process of claim 1 or 2, characterized in that the inorganic alkaline base is selected from the aqueous sodium and potassium hydrates.

4. The process of claim 1, characterized in that it is conducted at a temperature approximately ranging from 0° to 40° C.

5. The process of claim 1, characterized in being conducted at a temperature of about 20° C.

6. The process of claim 1, characterized in that the molar ratio between the inorganic alkaline base and methylthioacetaldoxime (II) is approximately comprised between 1:1 and 4:1.

7. The process of claim 1, characterized in that the molar ratio between the inorganic alkaline base and methylthioacetaldoxime (II) is maintained at about 3:1.

8. The process of claim 1, characterized in that the molar ratio between methylamine and methylthioacetaldoxime (II) is approximately comprised between 1:1 and 3:1.

9. The process of claim 1, characterized in that the molar ratio between methylamine and methylthioacetaldoxime (II) is maintained at about 2:1.

* * * * *